s006989004B2 -->

(12) United States Patent
Hinchliffe et al.

(10) Patent No.: US 6,989,004 B2
(45) Date of Patent: Jan. 24, 2006

(54) APPARATUS FOR DELIVERING ABLATION FLUID TO TREAT LESIONS

(75) Inventors: Peter W. J. Hinchliffe, Dowington, PA (US); James F. McGuckin, Jr., Radnor, PA (US); Stephan A. Defonzo, Wayne, PA (US)

(73) Assignee: Rex Medical, L.P., Conshohocken, PA (US)

( * ) Notice: Subject to any disclaimer, the term of this patent is extended or adjusted under 35 U.S.C. 154(b) by 131 days.

(21) Appl. No.: 10/145,863

(22) Filed: May 14, 2002

(65) Prior Publication Data
US 2002/0143302 A1 Oct. 3, 2002

Related U.S. Application Data

(63) Continuation-in-part of application No. 10/081,695, filed on Feb. 22, 2002, and a continuation-in-part of application No. 10/074,468, filed on Feb. 12, 2002.
(60) Provisional application No. 60/348,301, filed on Nov. 7, 2001, and provisional application No. 60/272,119, filed on Feb. 28, 2001.

(51) Int. Cl.
*A61M 5/178* (2006.01)

(52) U.S. Cl. .................. 604/164.01; 604/158; 604/187
(58) Field of Classification Search ................. 604/158, 604/187, 164.01, 164.04, 164.06, 164.07, 604/164.11, 165.01, 166.01, 272, 95.05, 264, 604/528
See application file for complete search history.

(56) References Cited

U.S. PATENT DOCUMENTS 4,013,080 A  3/1977  Froning

| | | |
|---|---|---|
| RE31,873 E | 4/1985 | Howes |
| 4,645,491 A | 2/1987 | Evans |
| 4,760,847 A | 8/1988 | Vaillancourt |
| 4,808,157 A | 2/1989 | Coombs |

(Continued)

FOREIGN PATENT DOCUMENTS

WO  WO 9846119  10/1998

OTHER PUBLICATIONS

Second Department of Internal Medicine, Faculty of Medicine, University of Tokyo, Japan, Gastroenterologia Japonica (JAPAN) Feb. 1991, p. 47–50, "Multiple–needle insertion method in percutaneous ethanol injection therapy for liver neoplasms", Shiina S; Hata Y; Niwa Y; Komatsu Y; Tanaka T; Yoshiura K; Hamada E; Ohshima M; Mutoh H; Kurita M; et al.

T.G. Frank, W. Xu and A. Cuschieri, "Instruments based on shape–memory alloy properties for minimal access surgery, interventional radiology and flexible endoscopy", 2000 (4 pages).

*Primary Examiner*—Kevin C. Sirmons
(74) *Attorney, Agent, or Firm*—Neil D. Gershon

(57) ABSTRACT

A surgical apparatus for delivering fluid to treat a lesion comprising an elongated member having a distal tip and a first and second set of openings formed in a sidewall proximal of the distal tip. The second set of openings is positioned proximally of the first set of openings. First and second set of fluid delivery members are movably positioned in the elongated for delivering fluid to the lesion. An actuator moves the fluid delivery members from a retracted position within the elongated members to a first deployed position extending radially with respect to the elongated member and moves the fluid delivery members from the first deployed position to a second deployed position extending further radially from the elongated member. The fluid delivery members are retained in the first and second deployed positions by a retention member.

18 Claims, 16 Drawing Sheets

U.S. PATENT DOCUMENTS

| | | | |
|---|---|---|---|
| 4,842,585 A | 6/1989 | Witt | |
| 4,846,799 A | 7/1989 | Tanaka et al. | |
| 4,869,259 A | 9/1989 | Elkins | |
| 4,926,860 A | 5/1990 | Stice et al. | |
| 4,958,901 A | 9/1990 | Coombs | |
| 5,067,957 A | 11/1991 | Jervis | |
| 5,102,396 A | 4/1992 | Bommarito | |
| 5,139,485 A | 8/1992 | Smith et al. | |
| 5,160,323 A | 11/1992 | Andrew | |
| 5,195,526 A | 3/1993 | Michelson | |
| 5,207,652 A | 5/1993 | Kay | |
| 5,215,527 A | 6/1993 | Beck et al. | |
| 5,231,989 A | 8/1993 | Middleman et al. | |
| 5,236,424 A | 8/1993 | Imran | |
| 5,242,448 A | 9/1993 | Pettine et al. | |
| 5,275,611 A | 1/1994 | Behl | |
| 5,354,279 A | 10/1994 | Höfling | |
| 5,360,416 A | 11/1994 | Ausherman et al. | |
| 5,385,148 A | 1/1995 | Lesh et al. | |
| 5,385,544 A | 1/1995 | Edwards et al. | |
| 5,403,311 A | 4/1995 | Abele et al. | |
| 5,405,376 A | 4/1995 | Mulier et al. | |
| 5,419,777 A * | 5/1995 | Hofling | 604/264 |
| 5,431,649 A | 7/1995 | Mulier et al. | |
| 5,435,805 A | 7/1995 | Edwards et al. | |
| 5,458,597 A | 10/1995 | Edwards et al. | |
| 5,464,395 A | 11/1995 | Faxon et al. | |
| 5,507,802 A | 4/1996 | Imran | |
| 5,558,673 A | 9/1996 | Edwards et al. | |
| 5,562,683 A | 10/1996 | Chan | |
| 5,562,687 A | 10/1996 | Chan | |
| 5,588,960 A * | 12/1996 | Edwards et al. | 604/20 |
| 5,599,345 A | 2/1997 | Edwards et al. | |
| 5,601,572 A | 2/1997 | Middleman et al. | |
| 5,607,389 A | 3/1997 | Edwards et al. | |
| 5,611,778 A | 3/1997 | Brinon | |
| 5,672,174 A | 9/1997 | Gough et al. | |
| 5,683,384 A | 11/1997 | Gough et al. | |
| 5,693,029 A | 12/1997 | Leonhardt | |
| 5,713,853 A | 2/1998 | Clark et al. | |
| 5,738,650 A | 4/1998 | Gregg | |
| 5,795,318 A | 8/1998 | Wang et al. | |
| 5,810,804 A | 9/1998 | Gough et al. | |
| 5,827,276 A | 10/1998 | LeVeen et al. | |
| 5,849,011 A | 12/1998 | Jones et al. | |
| 5,855,576 A | 1/1999 | LeVeen et al. | |
| 5,863,290 A | 1/1999 | Gough et al. | |
| 5,873,865 A | 2/1999 | Horzewski et al. | |
| 5,897,531 A | 4/1999 | Amirana | |
| 5,964,796 A | 10/1999 | Imran | |
| 5,980,517 A | 11/1999 | Gough | |
| 6,004,295 A | 12/1999 | Langer et al. | |
| 6,009,877 A | 1/2000 | Edwards | |
| 6,059,780 A | 5/2000 | Gough et al. | |
| 6,074,367 A | 6/2000 | Hubbell | |
| 6,080,150 A | 6/2000 | Gough | |
| 6,102,887 A | 8/2000 | Altman | |
| 6,106,521 A | 8/2000 | Blewett et al. | |
| 6,129,726 A | 10/2000 | Edwards et al. | |
| 6,132,425 A | 10/2000 | Gough | |
| 6,159,196 A | 12/2000 | Ruiz | |
| 6,179,813 B1 | 1/2001 | Ballow et al. | |
| 6,190,353 B1 | 2/2001 | Makower et al. | |
| 6,190,360 B1 | 2/2001 | Iancea et al. | |
| 6,200,274 B1 | 3/2001 | McNeirney | |
| 6,203,524 B1 | 3/2001 | Burney et al. | |
| 6,217,554 B1 | 4/2001 | Green | |
| 6,217,559 B1 | 4/2001 | Foster | |
| 6,221,049 B1 | 4/2001 | Selmon et al. | |
| 6,228,049 B1 | 5/2001 | Schroeder et al. | |
| 6,231,591 B1 | 5/2001 | Desai | |
| 6,254,573 B1 | 7/2001 | Haim et al. | |
| 6,280,424 B1 | 8/2001 | Chang et al. | |
| 6,283,951 B1 * | 9/2001 | Flaherty et al. | 604/529 |
| 6,302,870 B1 | 10/2001 | Jacobsen et al. | |
| 6,306,141 B1 | 10/2001 | Jervis | |
| 6,319,230 B1 | 11/2001 | Palasis et al. | |
| 6,346,095 B1 | 2/2002 | Gross et al. | |
| 6,425,887 B1 * | 7/2002 | McGuckin et al. | 604/272 |
| 6,428,517 B1 | 8/2002 | Hochman et al. | |
| 6,432,092 B2 | 8/2002 | Miller | |
| 6,511,458 B2 | 1/2003 | Milo et al. | |
| 6,730,061 B1 | 5/2004 | Cuschieri et al. | |

* cited by examiner

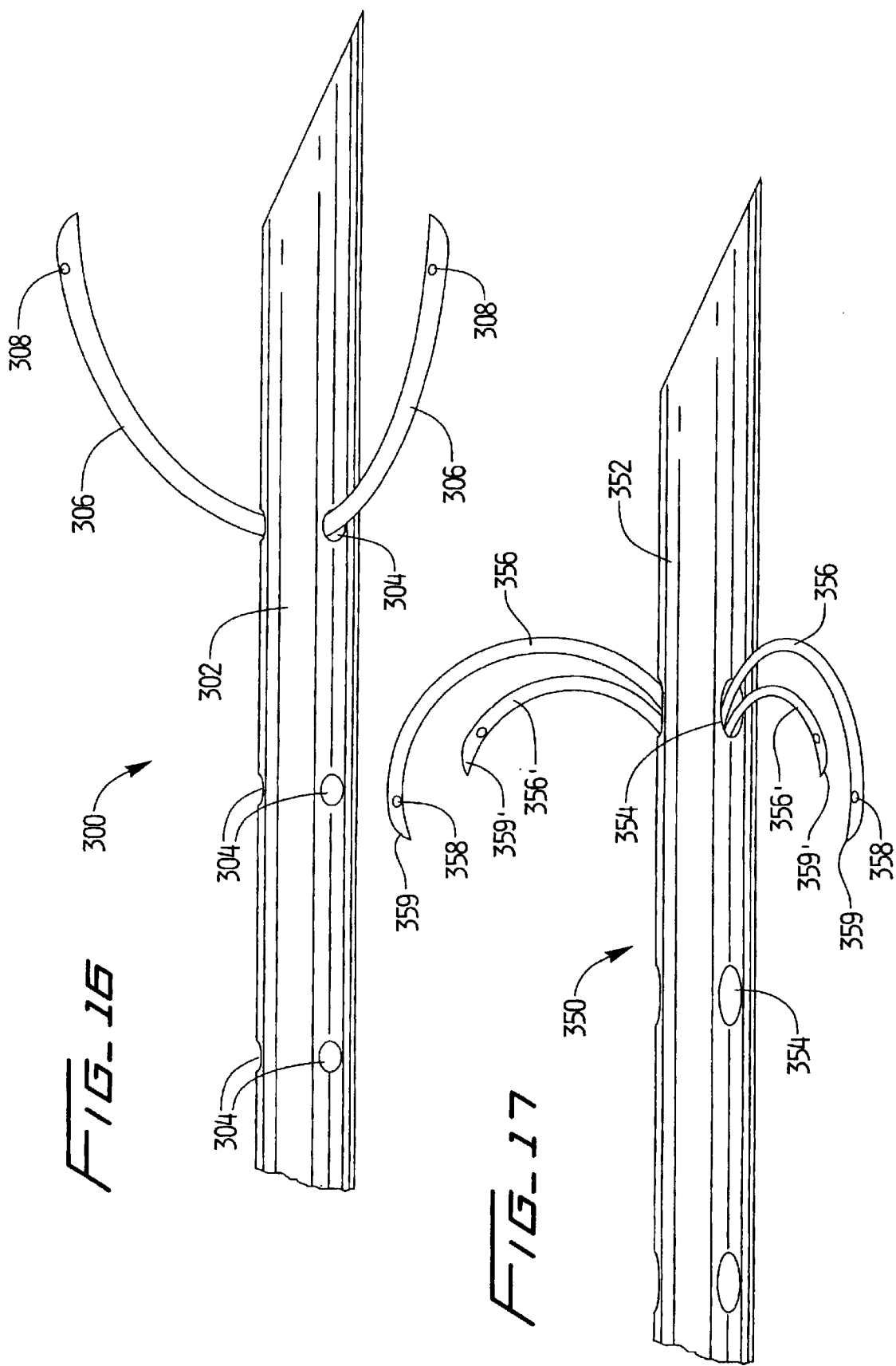

APPARATUS FOR DELIVERING ABLATION FLUID TO TREAT LESIONS

This application is a continuation-in-part of application Ser. No. 10/081,695, filed Feb. 22, 2002, which claims priority from provisional patent application Ser. No. 60/348,301, filed Nov. 7, 2001 and from provisional patent application Ser. No. 60/272,119 filed Feb. 28, 2001, and is a continuation-in-part of application Ser. No. 10/074,468, filed Feb. 12, 2002, which claims priority from provisional application No. 60/272,119, filed Feb. 28, 2001. The entire contents of each of these applications are incorporated herein by reference.

BACKGROUND

1. Technical Field

This application relates to a surgical apparatus for treating lesions and more particularly to an apparatus that delivers ablation fluid such as acetic acid or ethanol to ablate lesions.

2. Background of Related Art

One current method of treating hepatic (liver) cellular carcinomas is using electrosurgical energy in the form of radiofrequency energy. A series of electrodes are placed in the malignant tumor and a generator is activated to apply energy to the electrodes which heats the tissue to destroy the tumor. One example of such device is marketed by RITA Medical Systems which has an array of electrodes, offered in various configurations, which are curved outwardly from the tube in which they are constrained. It has been documented in the literature however that RF energy application is not consistently sufficient to ablate the cancerous tissue. Therefore, the patient must repeatedly return to the physician for additional applications of RF energy until the lesion is satisfactorily ablated. This not only adds to the expense of the procedure but can have an adverse psychological impact on the patient whose treatment is prolonged and characterized by frequent hospital visits. In additional to the clinical disadvantage, utilization of RF energy can be expensive since capital equipment, i.e. an RF generator for applying and controlling the electrosurgical energy, is required.

Another method of treating tumors is the injection of alcohol through a needle to ablate the tumor. The alcohol is typically about 95% to 99.5% ethanol and diffuses into the cancerous cells to produce immediate necrosis due to effects of cellular dehydration and protein denaturation followed by small vessel thrombosis.

One instrument currently being utilized to deliver ethanol to treat hepatic tumors is the Bernardino infusion needle, marketed by Cook of Bloomington, Ind. The needle is hollow and has two infusion ports adjacent the sharp distal tip. This device, however, has several disadvantages. The ethanol is injected only adjacent the distal tip, creating a relatively small treatment (ablation) zone. Therefore the needle must be repeatedly maneuvered and repositioned in various regions of the tumor and ethanol repeatedly injected until the entire tissue region has been treated. In fact, oftentimes the needle will have to be fully removed and reinserted into the patient, sometimes as frequently as twenty times in a single surgical procedure requiring twenty needle sticks, to ensure the entire region receives an adequate supply of ethanol.

Another method of treating tumors is the injection of acetic acid. The acetic acid has the additional advantage of penetrating the tumor septi and therefore providing more uniform chemical treatment of the lesion.

Commonly assigned co-pending application Ser. No. 10/074,468, filed Feb. 12, 2001, the entire contents of which are incorporated herein by reference, discloses an instrument for delivering ethanol, acetic acid, or other ablation fluid which advantageously avoids the aforedescribed multiple needle sticks and limited ablation zone. The instrument disclosed in the '119 application provides a larger treatment zone to ablate a larger tumor, avoids multiple needle sticks, reduces the time required for treatment, and simplifies the surgical procedure. Additionally, it provides a more uniform treatment zone as well as the ability to vary the treatment zone so that the same delivery needle could be adapted for different sized lesions.

Commonly assigned co-pending application Ser. No. 10/081,695, filed Feb. 22, 2002, the entire contents of which are incorporated herein by reference, discloses another instrument for delivering ablation fluid. The instrument achieves the objectives of providing larger and more uniform needle treatment zone, avoidance of multiple needle sticks, ability to vary the treatment zone and simplification of the procedure as in the needle of the '468 application, as well as provides a greater certainty of the location of the ablation needles and the boundary of the ablation zone.

The present application discloses alternative instruments for delivering ablation fluid to treat lesions which achieve the foregoing objectives.

SUMMARY

The present invention, like the apparatus of the commonly assigned co-pending patent applications referred to herein, overcomes the drawbacks and deficiencies of the prior art. The present invention advantageously provides a surgical apparatus for delivering fluid to treat a lesion comprising an elongated member having a distal tip and a first and second set of openings formed in a sidewall proximal of the distal tip. The second set of openings is positioned proximally of the first set of openings. First and second fluid delivery members are movably positioned in the elongated member wherein each of the fluid delivery members has a lumen and at least one opening communicating with the lumen for delivering fluid to the lesion. An actuator is operatively associated with the fluid delivery members and is actuable to a first position to move the fluid delivery members from a retracted position within the elongated members to a first deployed position extending radially with respect to the elongated member. The actuator is further actuable to a second position to move the fluid delivery members from the first deployed position to a second deployed position extending further radially from the elongated member. The fluid delivery members are retained in the first and second deployed positions by a retention member.

Preferably, the distal tip of the elongated member and the fluid delivery members are sharp to penetrate tissue. In one embodiment, the fluid delivery members are composed of stainless steel. In another embodiment, the fluid delivery members are composed of shape memory material.

In one embodiment the first and second fluid delivery members are extendable through the first set of openings and third and fourth fluid delivery members are extendable through the second set of openings, wherein the first and second fluid delivery members are positioned proximally of the third and fourth fluid delivery members. The apparatus may further comprise an indicator to indicate the deployed positions of the fluid delivery members.

In another embodiment, third and fourth fluid delivery members are provided wherein the first and second fluid delivery members are extendable through one opening of the first set of openings and the third and fourth fluid delivery members are extendable through another opening of the first set of openings Preferably, the actuator is movable axially to move the fluid delivery members to the deployed position and the fluid delivery members are connected to an elongated tube operatively connected to the actuator. In one embodiment, movement of the actuator substantially simultaneously moves the first and second fluid delivery members through the first set of openings and the third and fourth fluid delivery members through the second set of openings. In another embodiment, the actuator is movable to first and second axial positions, wherein in the first axial position the first and second fluid delivery members are deployable through the first set of openings and in the second axial position the first and second fluid delivery members are deployable through the second set of openings.

The present invention also provides a surgical apparatus for delivering fluid to treat a lesion comprising an elongated member having a distal tip and a first and second set of openings formed in a sidewall proximal of the distal tip wherein the second set of openings is positioned proximally of the first set of openings. A plurality of fluid delivery members are movably positioned in the elongated member, each of the fluid delivery members having a lumen and at least one opening communicating with the lumen for delivering fluid to the lesion. An actuator is operatively associated with the fluid delivery members. The actuator is actuable to a first position to move the fluid delivery members from a retracted position within the elongated member to a first deployed position extending through the first set of openings and radially with respect to the elongated member to treat a first portion of the lesion. The actuator is further actuable to a second position to move the fluid delivery members to a second deployed position extending through the second set of openings and radially with respect to the elongated member to treat a second portion of the lesion proximal of the first portion.

Preferably, the apparatus includes a ratchet cooperating with the actuator and slidable distally and proximally. The actuator may include a tab engagable with the ratchet and extendable through a respective opening in the ratchet and the ratchet may have a tab to retain the fluid delivery members in one of the first and second positions.

The elongated member may comprise a third set of openings positioned proximally of the second set of openings wherein the actuator is actuable to a third position to move the fluid delivery members through the third set of openings. The fluid delivery members are preferably movable to a plurality of radial positions with respect to the elongated member through each set of openings.

The apparatus may further comprise an indicator to provide an indication of the deployed positions and the radial positions of the fluid delivery members.

In one embodiment, multiple fluid delivery members extend through each opening of the sets of openings, and the fluid delivery members extending through each opening have a different radius of curvature.

The present invention also provides a surgical apparatus for delivering fluid to treat a lesion comprising an elongated member having a distal tip and a plurality of openings formed in a sidewall proximal of the distal tip. A plurality of fluid delivery members are rotatably positioned in the elongated member, and each of the fluid delivery members has a lumen and at least one opening communicating with the lumen for delivering fluid to the lesion. A rotatable actuator is operatively associated with the fluid delivery members.

The actuator has a plurality of threads and is rotatable to a first position to move the fluid delivery members from a retracted position within the elongated member to a first position extending through the plurality of openings and radially with respect to the elongated member, and actuable to a second position to move the fluid delivery members to a second deployed position extending further radially with respect to the elongated member than the first deployed position.

Preferably, when in the first and second deployed positions, the fluid delivery member remains proximal of the distalmost tip of the elongated member. An indicator can also be provided to provide an indication of the deployed and radial position of the fluid delivery members.

BRIEF DESCRIPTION OF THE DRAWINGS

Preferred embodiment(s) of the present disclosure are described herein with reference to the drawings wherein:

FIG. 16 is a side view of a distal portion of the apparatus of another alternate embodiment having fluid delivery members extending in a distal direction when deployed; and FIG. 17 is a perspective view of a distal portion of yet another alternate embodiment of the apparatus of the present invention having multiple fluid delivery members extending through each of the windows of the needle.

DETAILED DESCRIPTION OF PREFERRED EMBODIMENTS

Figure 1:
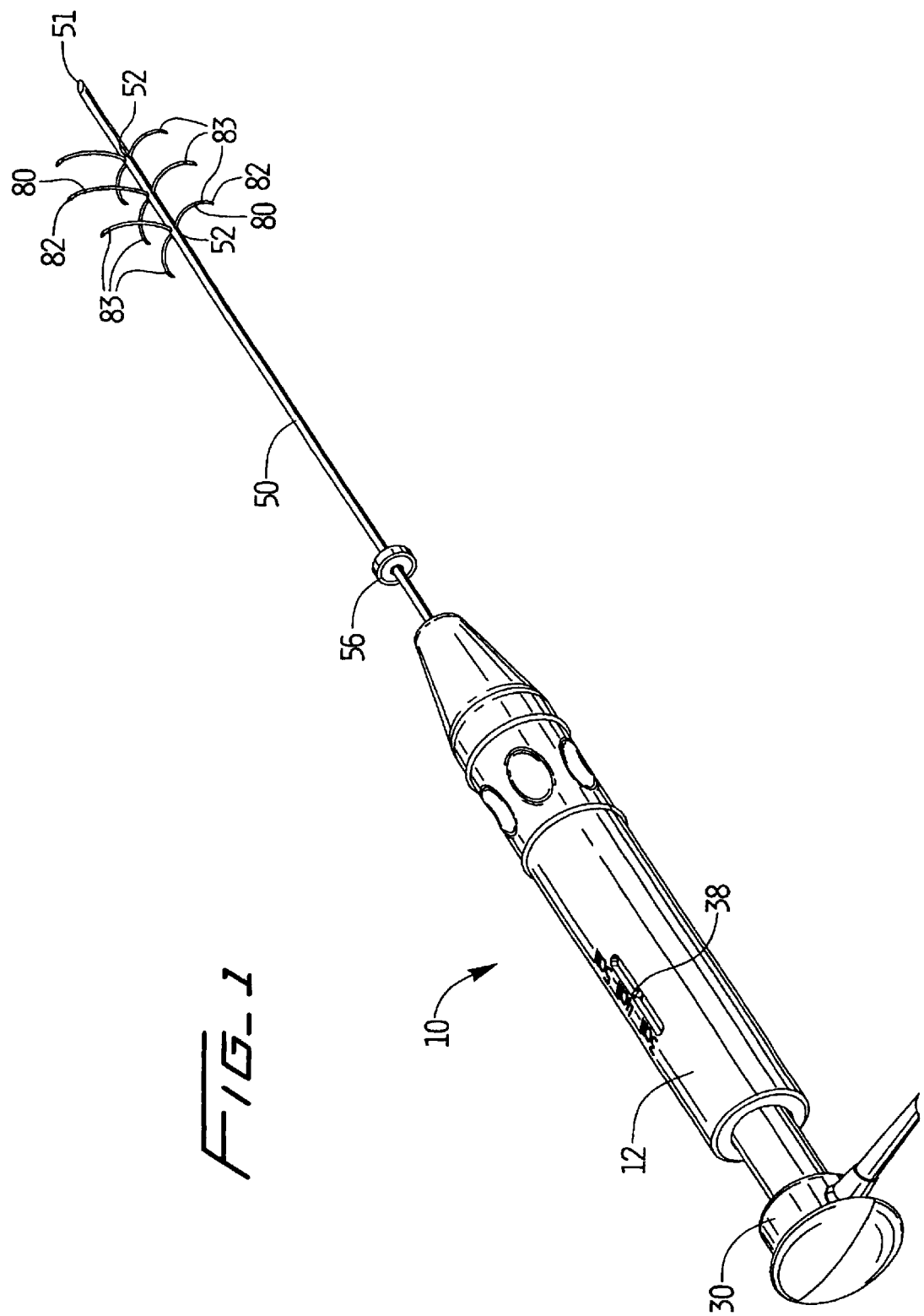
FIG. 1 is a perspective view of a first embodiment of the apparatus of the present invention showing the fluid delivery members (tines) in the fully deployed position.

Referring now in detail to the drawings where like reference numerals identify similar or like components throughout the several views, a first embodiment of the apparatus of the present invention for delivering fluid for tumor ablation is designated generally by reference numeral 10 and illustrated in FIG. 1. Apparatus 10 includes a housing or body 12, an actuator or plunger 30, and an elongated tubular member or needle 50 extending distally from the housing 12. A plurality of fluid delivery members or tines 80 (only a few are labeled for clarity) are extendable from the needle 50, in response to movement of the plunger 30, to deliver acetic acid, ethanol, or other ablation fluid to the target tissue. The tines 80 extend through respective side windows (openings) 52 formed in the needle 50, and each tine 80 contains openings 83 in the sidewall communicating with a lumen formed therein. The side windows 52 in needle 50 extend axially along a portion of the length of the needle 50 to enable simultaneous delivery of fluid through the tines 80 to a large lesion area. When deployed as shown in FIG. 1, the distal ends 82 of the tines 80 remain proximal of the distal tip of the needle 50, thereby controlling the zone of acetic acid delivery and thus the zone of tissue ablation. (Note that for clarity only a few of the tines 80, side windows 52 and openings 83 are labeled in FIG. 1.)

Figure 2:
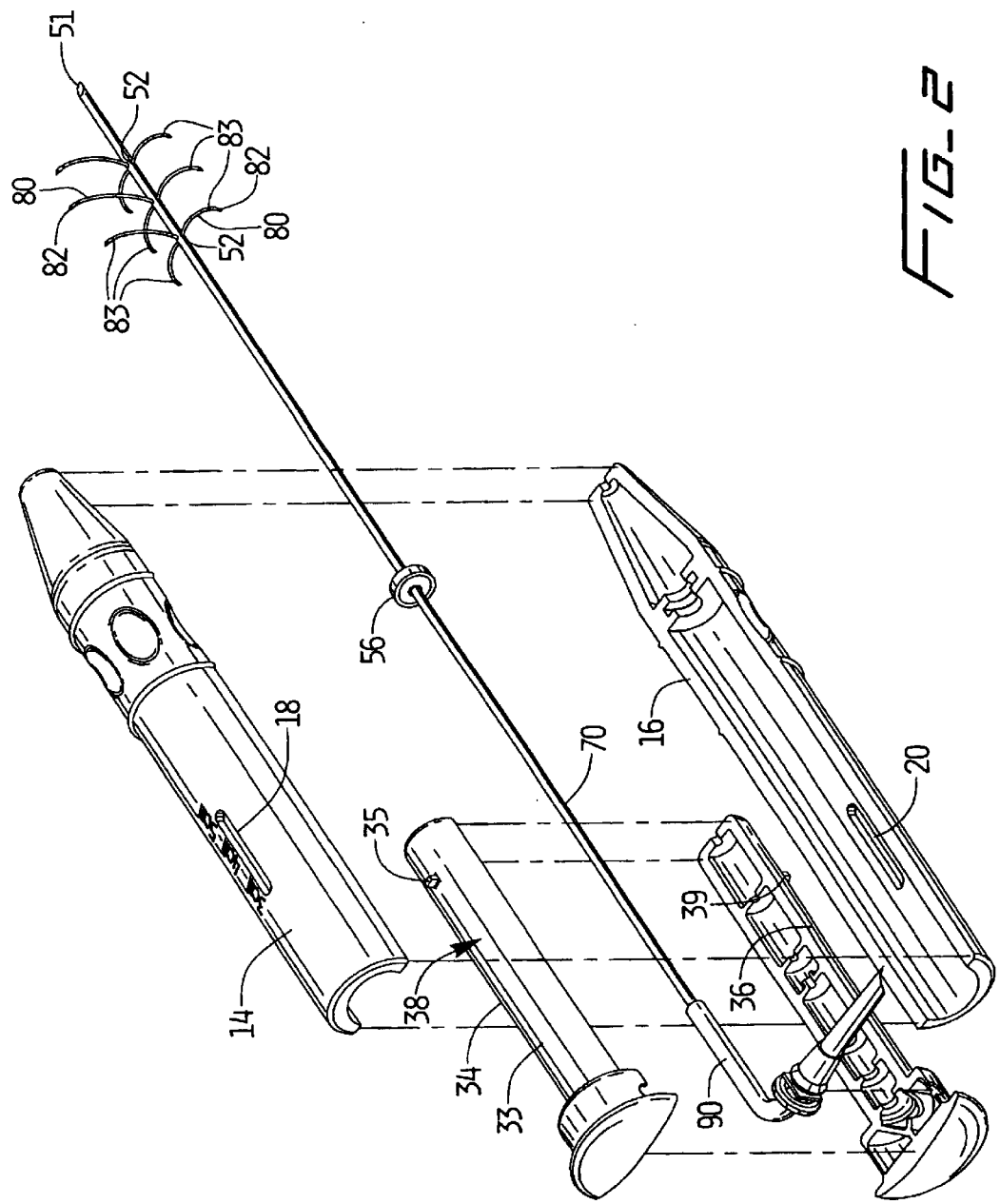
FIG. 2 is an exploded view of the apparatus of FIG. 1.

With reference to FIGS. 1 and 2, details of the apparatus 10 will now be described. Housing 12 is composed of first housing half 14 and identical second housing half 16 and plunger 30 is composed of first plunger half 34 and identical second plunger half 36. An elongated window 18, 20 is formed in each housing half 14, 16 to indicate the extent of distal movement of the plunger 30 and thus the deployment position of the tines 80. In the embodiment illustrated, numerical markings designating "3 cm, 4 cm, 5 cm" indicate the radial dimension of the ablation zone created by the tines 80 in the corresponding position. For example, in FIG. 1, tab 38 of plunger 30 is located at the area marked "4 cm" to indicate the tines 80 are deployed to create a 4 mm ablation zone. Clearly, other markings to indicate the tine position as well as other measurements could be utilized.

As an alternative to tab 38, it should be appreciated that other types of indicators are also contemplated such as a pad printed dot as described in the commonly assigned co-pending applications incorporated herein by reference.

Figure 3:
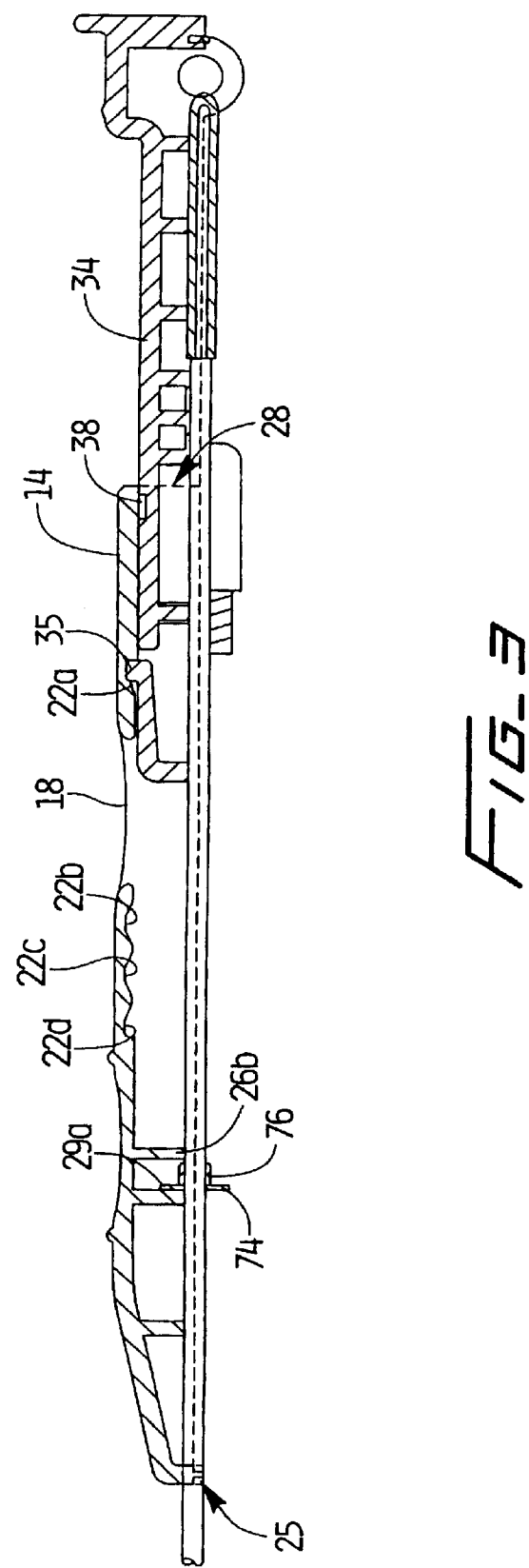
FIG. 3 is a longitudinal sectional view of the first plunger half and first housing half showing the actuator in the initial position.

Also extending from the outer surface 33 of plunger half 34 is a flexible retention tab 35, best shown in FIGS. 2 and 3. Retention tab 35 is positionable in one of the recesses 22a–22d of first housing half 14, depending on the position of the tines 80 with respect to the needle 50. An identical retention tab 39 engages respective recesses (not shown) on second housing half 16. Retention tabs 35, 39 help to retain the plunger 30 and therefore the tines 80 in position as well as provide a tactile feel to the user of the positions of tines 80.

In the initial position of the plunger 30, retention tab 35 is in proximal recess 22a and indicator tab 38 is not visible in window 18. When the plunger 30 is advanced to the first position to advance the tines 80 to a first deployed position, retention tab 35 is retained within recess 22b and indicator tab 38 is visible in the proximal area of the window, e.g. corresponding to the "3 cm" deployment marking. When the plunger 30 is further advanced axially, retention tab 35 is moved into recess 22c, corresponding to deployment of the tines 80 a further radial distance from needle 50. Indicator tab 38 would then be visible at the intermediate "4 cm" marking. Full advancement of the plunger 30 moves retention tab 35 into engagement within distal recess 22d, corresponding to full deployment of the tines 80 with the indicator tab 38 visible at the "5 cm" marking. The indicator tab of second plunger half 36 would function to appear in window 20 of second housing half 16 and the retention tab 39 of second plunger half 36 would function to engage recesses (not shown) in the second housing half 16 in an identical manner as tabs 38 and 35 of first plunger half 34.

Figure 4A:
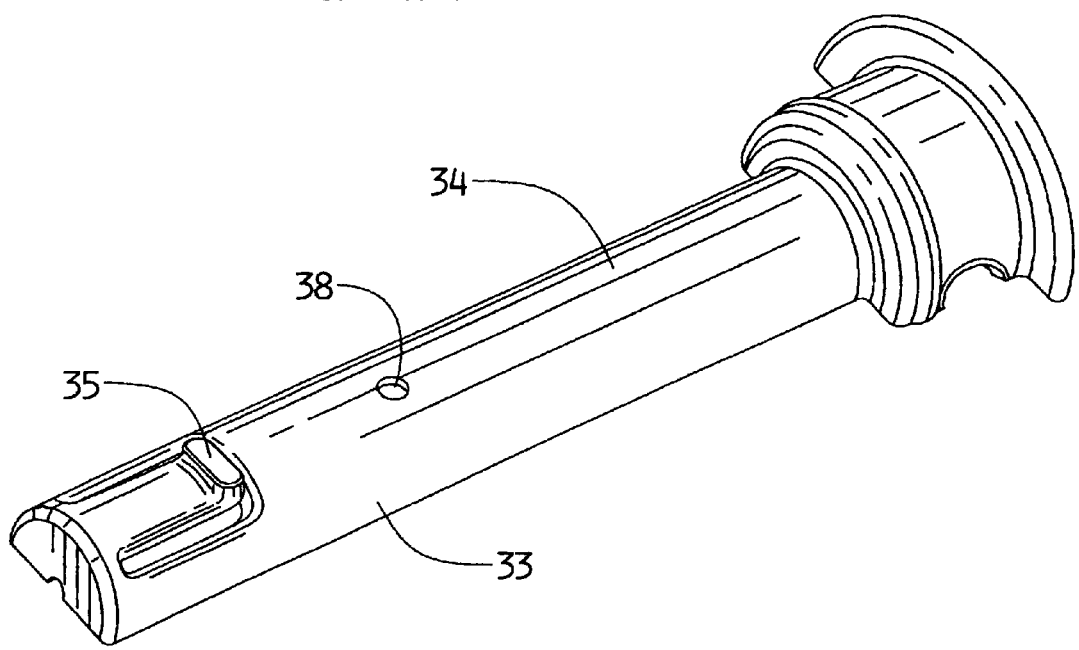
FIG. 4A is a perspective view of the first plunger half of the apparatus of FIG. 1.
Figure 4B:
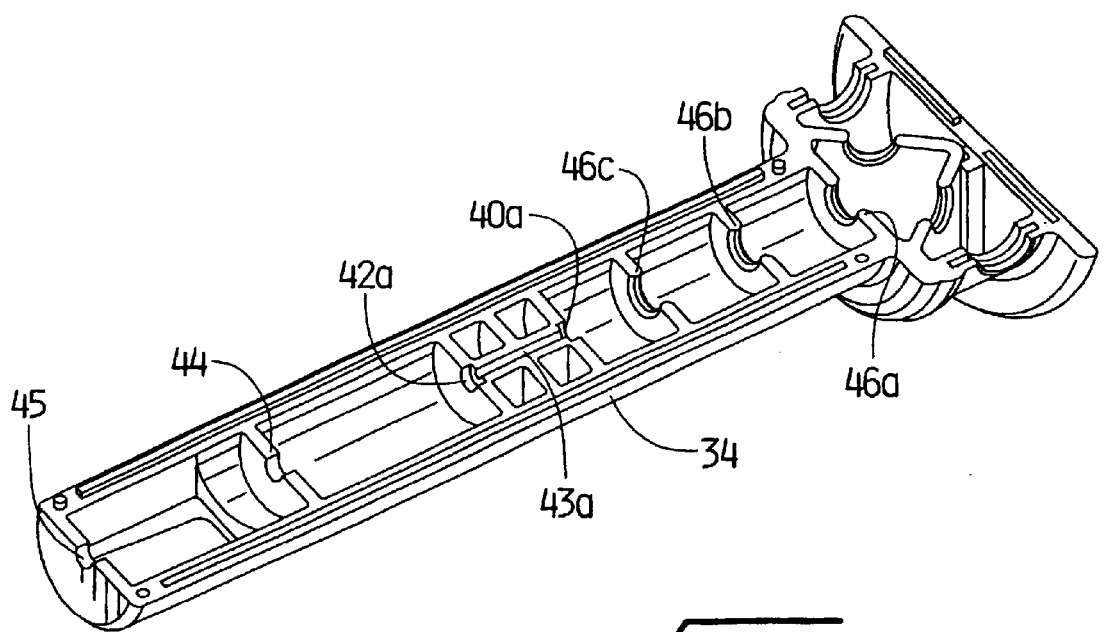
FIG. 4B is a perspective view-of the first plunger half of FIG. 4A rotated 180 degrees.
Figure 5:
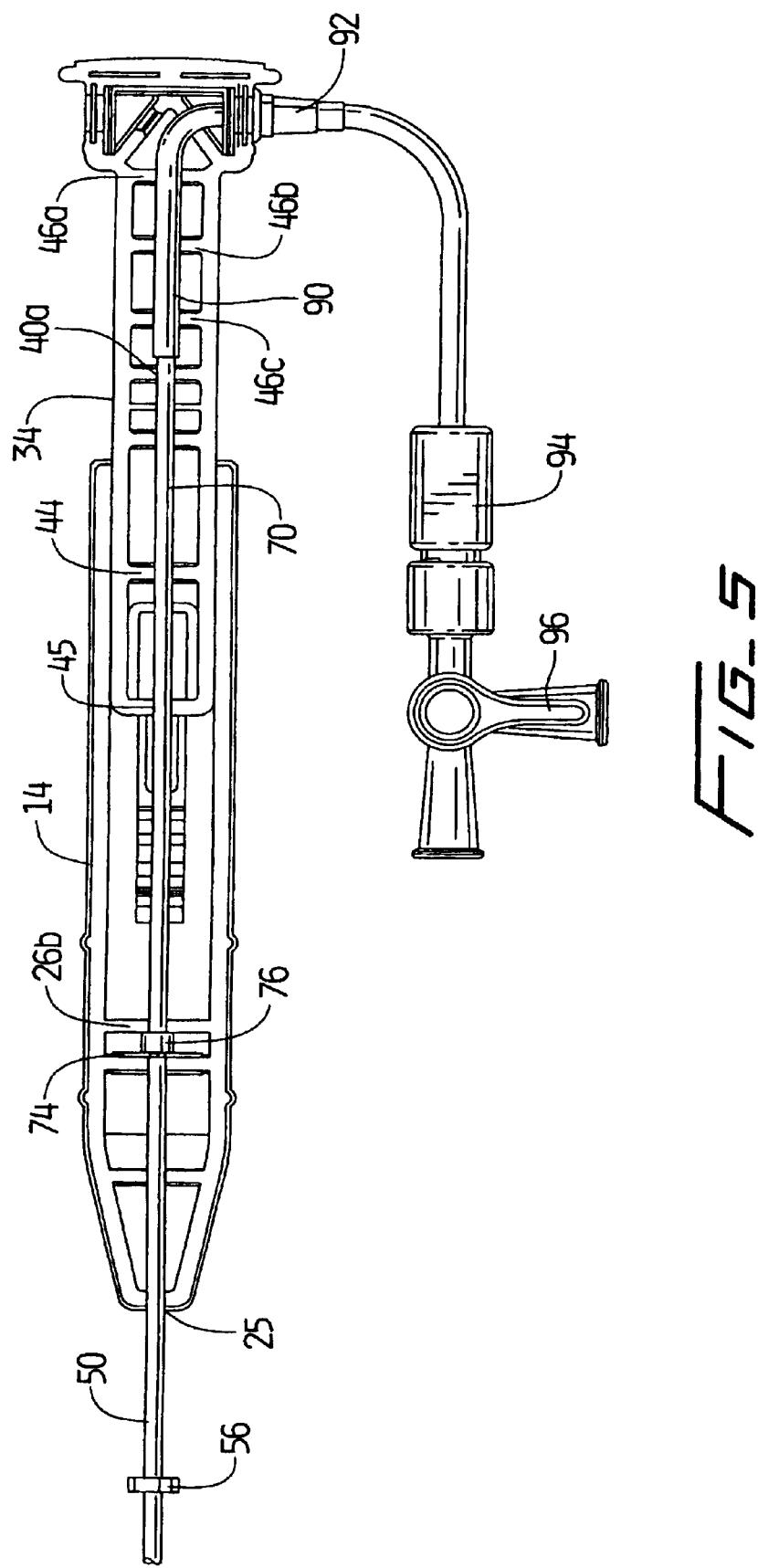
FIG. 5 is a top view of the apparatus of FIG. 1, with the second plunger half and second housing half removed to illustrate retention of the tubing and needle.

For clarity, some of the ribs and recesses of the plunger 30 for retaining the inner tube 70 and tubing 90 are omitted from the exploded view of FIG. 2; however they are shown in the perspective view of first plunger half 34 in FIG. 4B. With reference to FIGS. 4 and 5, tubing 90 is seated within ribs 46a, 46b and 46c of first plunger half 34 which cooperate with identical ribs (not shown) of plunger half 36. Tubing 90 terminates at a distal end proximal of pocket 40a (and corresponding pocket of plunger half 36) where it is frictionally fit over inner tube 70 to provide fluid communication between the lumen of tubing 90 and the lumen of inner tube 70. As shown in FIG. 5, tubing 90 is attached at a proximal end to luer fitting 94. Strain relief 92 is frictionally retained over tubing 90 to limit kinking of the tubing. Stopcock 96 controls ablation fluid flow and saline flow for the reasons described below.

Distal round pockets 40a, 42a and elongated squared pocket 43a formed therebetween in plunger half 34 cooperate with corresponding round and square pockets on plunger half 36 to mount support (inner) tube 70. The tines 80 are attached to inner tube 70 by gluing, welding or other means. Inner tube 70 both transports fluid to the lumens of the tines 80 from tubing 90 as well as moves the tines 80 between their retracted and deployed positions. A seal block 76, sandwiched between needle retention plate 74 and wall 26b, prevents leakage proximally between the needle 50 and inner tube 70. Needle 50 extends through distal opening 25 of housing 12.

It should also be appreciated that alternatively the plunger configuration described and shown in FIGS. 26–32 of the '695 application, incorporated herein by reference, utilizing for example a tube retention plate, could be utilized.

Referring back to FIGS. 1 and 2, the needle 50 preferably contains three sets of openings each set spaced axially from the other sets along the distal portion of needle 50. Each set preferably contains three radially spaced openings, each forming an exit aperture (side window) 52 for a respective tine 80. Upon advancement of plunger 30, all nine tines 80 are moved from a substantially straight position within needle 50 (substantially aligned with the longitudinal axis of the needle 50) to a curved position extending radially from the needle 50 through windows 52. The extent of radial deployment will depend on the position of the plunger 30 as described above, i.e. the further axial distal advancement of the plunger 30, the further radial advancement of tines 80. Once deployed, ablation fluid such as acetic acid can be injected through tubing 90, inner tube 70, and through tines 80, exiting openings 83 in the sidewall of each tine. Preferably three sidewall openings 83 are provided in each tine, but fewer or greater number are also contemplated. The use of multiple tines spaced radially and axially enables a larger and longer treatment zone to be created with a single position of the apparatus 10.

Clearly a different number of tines (and corresponding needle windows) could be provided as well as a different number of side openings in the tines for fluid flow. If shape memory tines 80 are utilized, the infusion of cold saline will maintain the tines 80 in the martensitic state to facilitate passage from the needle 50 as described in the '695 and '468 applications. Stainless steel tines are also contemplated.

A marking ring 56 is mounted on needle 50 to provide a depth indicator for apparatus 10. A series of markings (not shown) are provided along the length of the needle 50 on the outer surface, visible to the user, to indicate the depth of penetration, i.e. the distance from the distal tip 51 of the needle 50 to the marking ring 56. Prior to insertion, the surgeon slides the marking ring 56 along the needle length to align with the desired depth marking. This would define the extent of penetration since the surgeon would insert the apparatus 10 until resistance was felt by the marking ring 56 against the skin. Thus, the depth of penetration could be predetermined and better controlled.

FIGS. 6–12 illustrate a second embodiment of the fluid delivery apparatus of the present invention, designated generally by reference numeral 110. Apparatus 110 includes a housing or body 112, an actuator or plunger 130, and an elongated tubular member or needle 150 extending distally from the housing 112 through distal opening 125. The three fluid delivery tines 180a, 180b and 180c are extendable from the needle 150 through any of the three sets of windows in response to movement of the plunger 130. The tines 180, like tines 80 described above, contain openings for delivery of acetic acid, ethanol, or other ablation fluid to the target tissue. The tines 180 are also shown deployed to a position wherein their distal ends remain proximal of the distal tip 151 of the needle 150, thereby controlling the zone of acetic acid (or other ablation fluid) delivery and thus the zone of tissue ablation.

Figure 6:
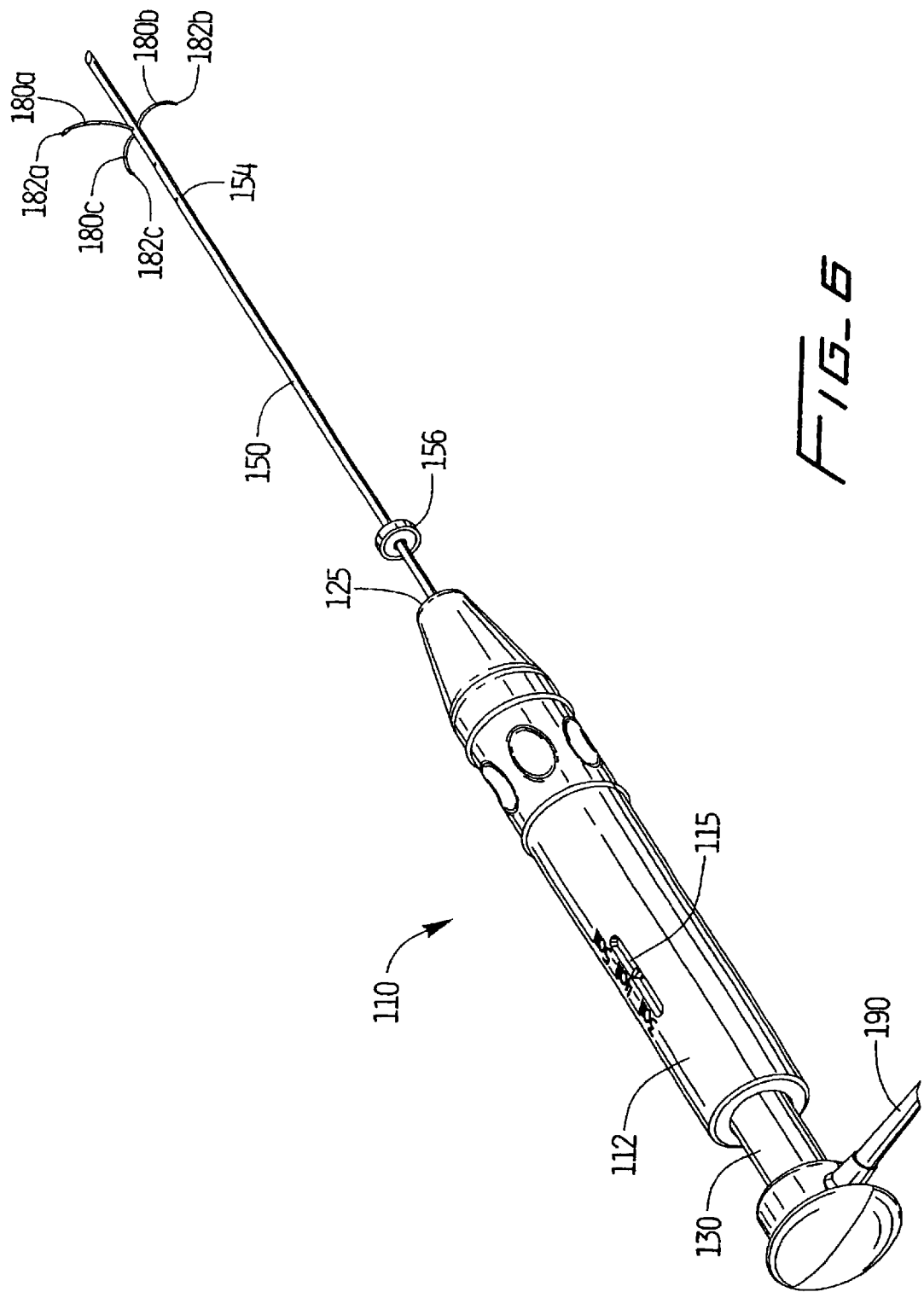
FIG. 6 is a perspective view of an alternate embodiment of the apparatus of the present invention showing the fluid delivery members (tines) in the fully deployed position.

More specifically, needle 150 has three sets of windows (openings) 152, 153, and 154 forming exit apertures for the tines 180. The windows (openings) of each set are preferably radially spaced around the needle 150; the sets of windows are axially spaced as shown. Three tines 180a, 180b, 180c are contained within the needle 150 in a substantially straight retracted position substantially parallel to the longitudinal axis of the needle 150, and are deployable radially from the needle 150 through one of the sets of windows, 152, 153, 154, depending on the position of the plunger 130. The tines 180 are shown in FIG. 6 extending from the distal set of apertures 152. Each of the tines 180a–180c has a sharp distal tip 182a–182c, respectively, for penetrating tissue and a series (preferably three) of openings 181a–181c (see e.g. FIG. 9) in the sidewall communicating with its internal lumen to deliver ablation fluid.

Although three sets of windows, each containing three apertures, are illustrated, it is contemplated that fewer or greater number of windows (apertures) can be provided in each set and fewer or greater set of windows (apertures) could be provided. Additionally, fewer or greater number of fluid delivery tines as well as sidewall openings in the tines could be provided.

Figure 7:
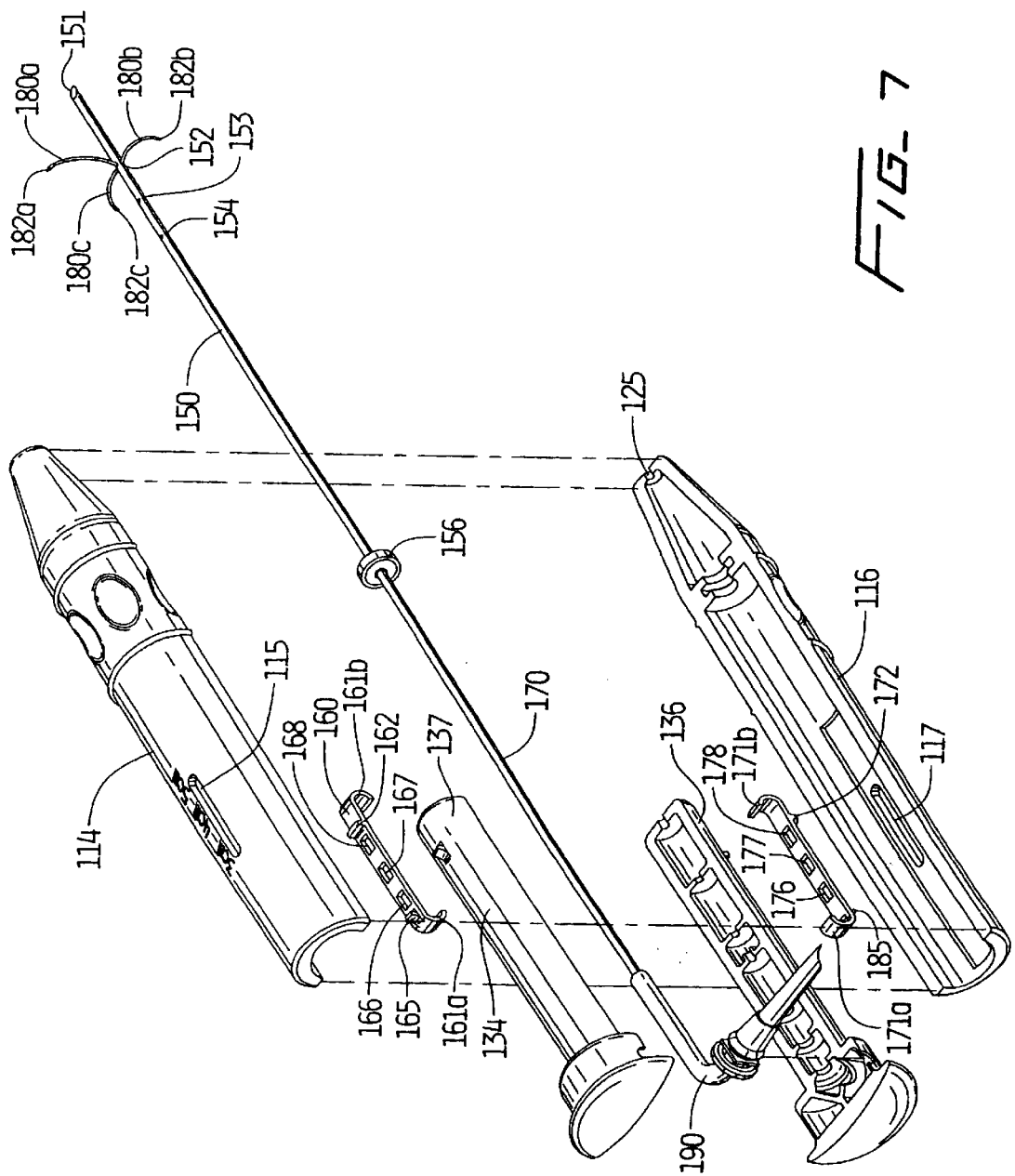
FIG. 7 is an exploded view of the apparatus of FIG. 6.
Figure 8:
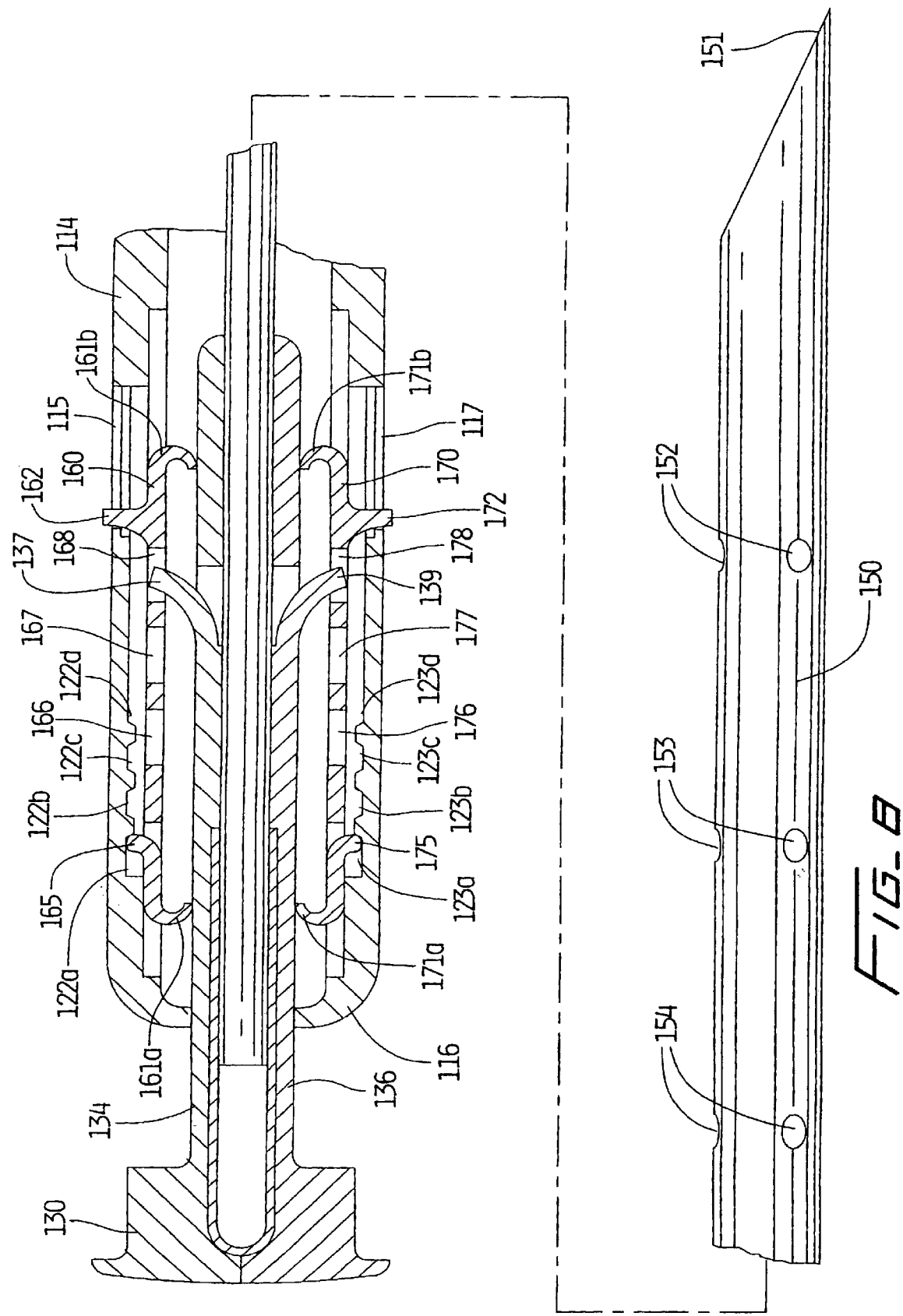
FIG. 8 is a longitudinal cross-sectional view of the actuation portion of the apparatus of FIG. 6 showing the plunger in the retracted position and the ratchet in the initial position, and further showing a side view of the distal portion of the apparatus (with the tines fully retracted within the needle)

Turning now to details of the apparatus, and with reference to the exploded view of FIG. 7 and the longitudinal cross-sectional view of FIG. 8, housing 112 is formed of first and second housing halves 114, 116 and actuator (plunger) 130 is formed of first and second plunger halves 134, 136. First and second ratchets 160, 170 are interposed between respective housing and plunger halves as shown. Ratchet 160 has an indicator tab 162 which extends through indicator window 115 of housing half 114. Similarly, ratchet 170 has an indicator tab 172 extending through indicator window 117 of housing half 116.

Flexible retention member or tab 165 first ratchet 160 is engagable with a respective recess 122a–122d in housing 114 and flexible retention member or tab 175 of ratchet 170 is engagable with a respective recess 123a–123d in housing half 116. The retention tabs 165, 175 function to retain the plunger 130 in one of four positions corresponding to the extent of radial deployment of the tines 180. This is explained in more detail below in conjunction with the operation of the instrument.

Also formed in ratchets 160, 170 are three apertures 166, 167, 168, and 176, 177, 178, configured to receive actuator tabs 137, 139 of first and second plunger halves 134, 136, respectively, for movement of the ratchets as described below.

Support tube 190 and inner tube 170 can be supported within plunger halves 134, 136 in a similar manner as described above in conjunction with the first embodiment. Thus, ribs, locking plates, etc. can be provided and have been omitted from FIG. 7 for clarity.

Inner tube 170 is connected to tines 180 for moving the tines as well as for transport of ablation fluid. That is, inner tube 170 is in fluid communication with tubing 190 and with the lumens of tines 180 to deliver ablation fluid to the tines 180 in a similar manner as described above with respect to inner tube 70, tubing 90 and tines 80 of the embodiment of FIG. 1.

If shape memory tines 80 are utilized, the infusion of cold saline will maintain the tines 80 in the martensitic state to facilitate passage from the needle 150 as described in the '695 and '468 applications. Stainless steel tines are also contemplated.

The operation of the plunger 130 and ratchets 160, 170 to advance the tines 180 through the windows 152, 153, 154 in the needle 150 will now be described. FIG. 8 shows in cross-section the interaction of the first plunger half 134 and ratchet 160 with first housing half 114 and the interaction of the second plunger half 136 and ratchet 170 with second housing half 116 when the device is in its initial position. In this initial position, the tines 180 are fully retracted within the needle 150 and are therefore not seen in FIG. 8.

As shown, in this initial position of the instrument, plunger 130 is in the retracted position with plunger tab 137 of first plunger half 134 extending through distal aperture 168 in ratchet 160 and plunger tab 139 of second plunger half 136 extending through distal aperture 178 in ratchet 170. With tabs 137 and 139 in this position of the ratchets, deployment of the tines 180 will occur through distal windows 152 of needle 150. Note in this initial position, retention tabs 165 and 175 of ratchets 160, 170 are engaged in recess 122a of housing half 112 and recess 123a of housing half 116, respectively. Indicator tabs 162, 172 of ratchets 160, 170 are in the proximalmost portion of the respective windows 115, 117 of housing halves 114, 116, indicating to the user that the tines 180 are in their retracted position.

In this retracted position, the apparatus 110 is inserted into the patient so the distal tip 151 of the needle 150 is adjacent (or slightly past) the region of tissue to be treated. Note that depth marker 156 (FIG. 6) can be preset to set the depth in the same manner as marker 56 of FIG. 1 to control the depth of needle insertion.

Figure 9:
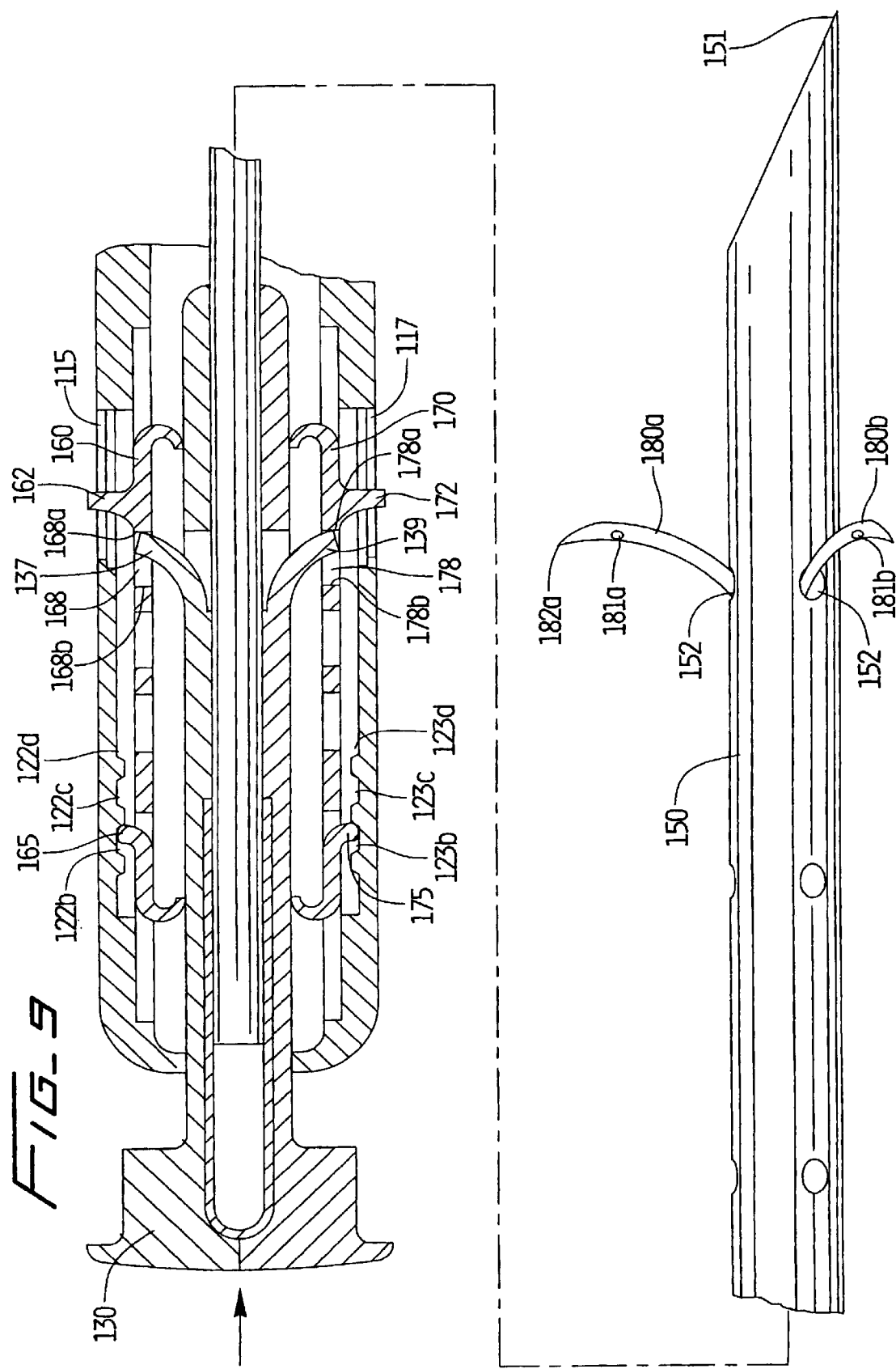
FIG. 9 is a longitudinal cross-sectional view similar to FIG. 8 except showing the ratchet advanced as the plunger is moved distally and the tines deployed to a first position through the distal windows of the needle.
Figure 10:
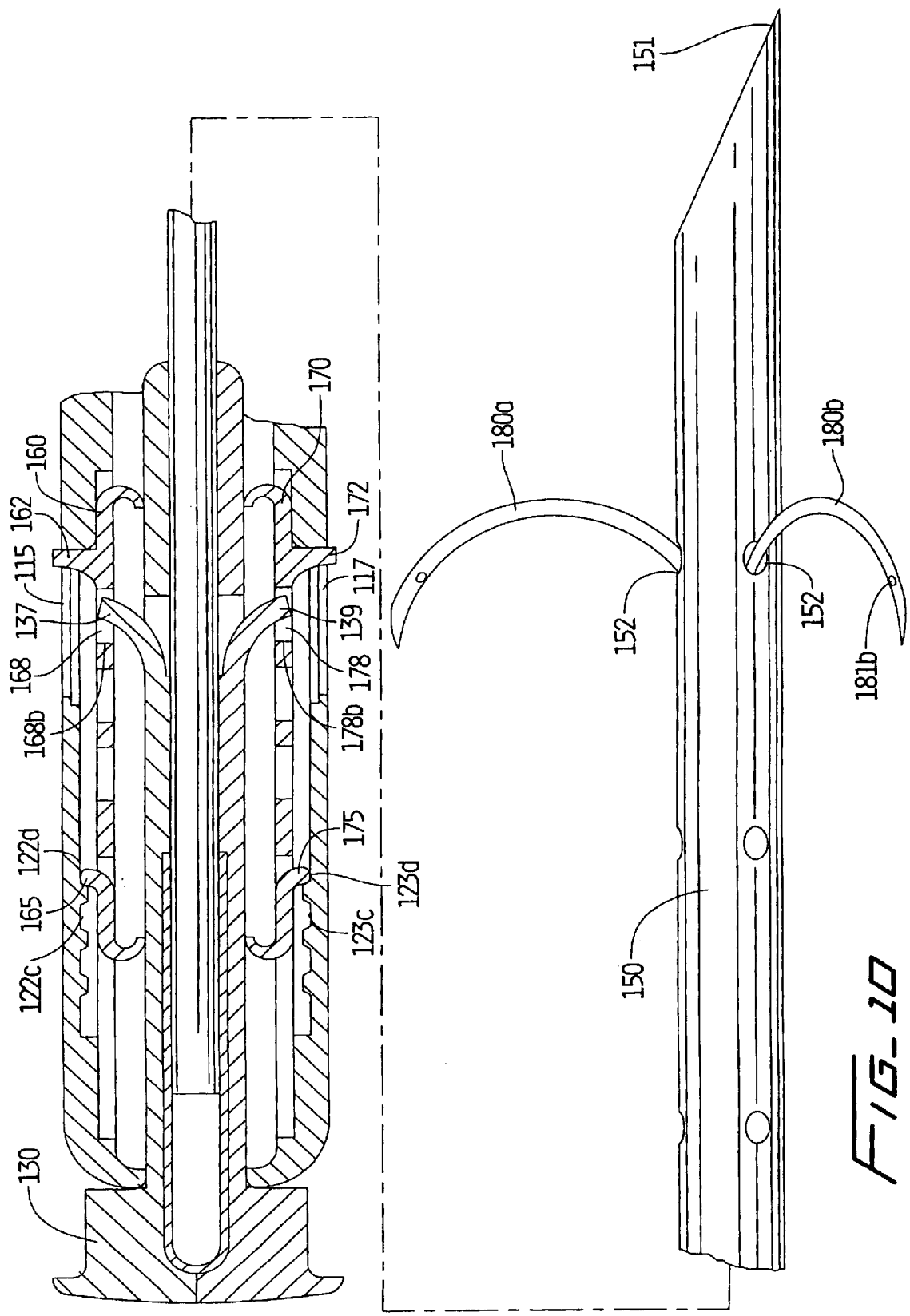
FIG. 10 is a longitudinal cross-sectional view similar to FIG. 8 except showing the plunger (and ratchet) in an advanced position and the tines advanced to a fully deployed position through the distal windows of the needle.

Once at the desired site, plunger 130 is advanced distally, sliding ratchets 160 and 170 in the direction of the arrow (FIG. 9) as actuator tabs 137, 139 abut edges 168*a*, 178*a* of distal apertures 168, 178 (see FIG. 9). Plunger 130 is slid until the flexible retention tabs 165, 175 engage recesses 122*b*, 123*b*, thereby retaining the tines 180 in a first deployed position (FIG. 9), extending through distal windows 152 radially with respect to the longitudinal axis of the needle 150. In this position, indicator tabs 162, 172 have moved to a position in respective windows 114, 115 to indicate to the user deployment of the tines 180 to a first deployed position. Further radial deployment of the tines 180 through distal windows 152 can be achieved by further distal advancement of the plunger 130 until retention tabs 165, 175 engage recesses 122*c*, 123*c*, to deploy the tines 180 to an intermediate (or second deployed) position. Still further distal movement of plunger 130 moves retention tabs 165, 175 into engagement with recesses 122*d*, 123*d* to deploy the tines to a third or fully deployed position through the distal windows 152 of the needle 150, as shown in FIG. 10. As the plunger 130 moves the tines 180 to the various radially deployed positions, their positioning is reflected by the position of indicator tabs 162, 172 in windows 115, 117. For example, as shown in FIG. 10, indicator tabs 162, 172 are in the distalmost region of the windows 115, 117, to indicate full radial deployment of the tines 180.

Figure 11:
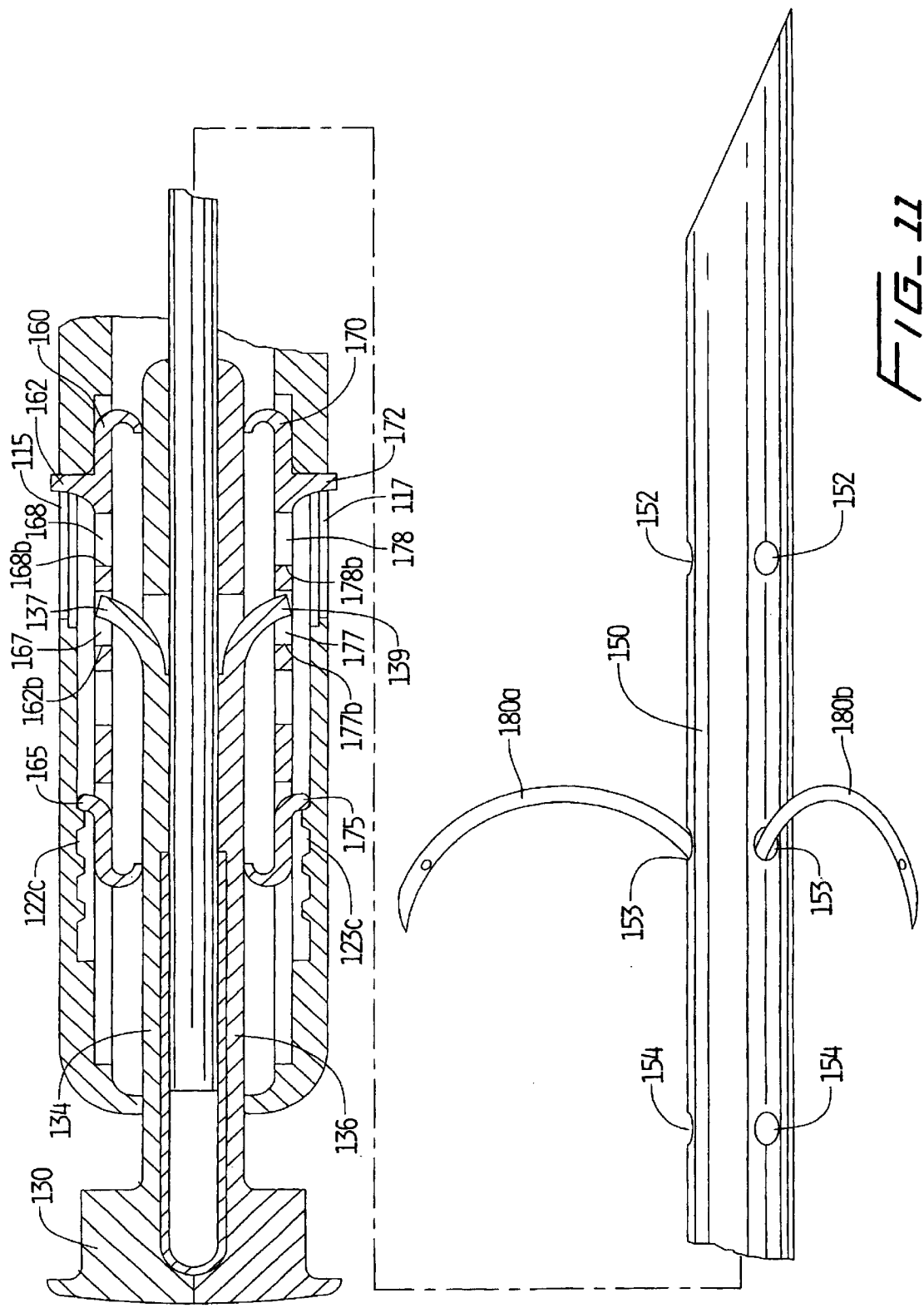
FIG. 11 is a longitudinal cross-sectional view similar to FIG. 8 except showing the plunger engaging the intermediate openings in the ratchet and in an advanced position and the tines advanced to a fully deployed position through the intermediate windows of the needle.

After ablation fluid is injected through the tines 180 at one or more of their three radial positions, the plunger 130 is retracted in a proximal direction, thereby pulling ratchets 160, 170 rearwardly, as respective plunger tabs 137, 139 engage the walls 168*b*, 178*b* of the distal apertures 168, 178. Once the plunger 130 is fully retracted, plunger tabs 137, 139 will slide out of distal apertures 168, 178 and slide into intermediate apertures 167, 177 (see FIG. 11). The plunger 130 can then be advanced distally to deploy the tines 180 radially through intermediate windows 153 in needle 150, with the flexible retention tabs 165, 175 engaging the respective recesses 122*a*–122*d*, 123*a*–123*d* to retain the plunger 130 and tines 180 in the first, second and third deployed positions. The indicator tabs 162, 172 would be visible in windows 115 and 117 to indicate the radial position of the tines 180. FIG. 11 illustrates the plunger 130 in the distalmost position corresponding to full deployment of tines 180 through intermediate windows 153 of needle 150.

Figure 12:
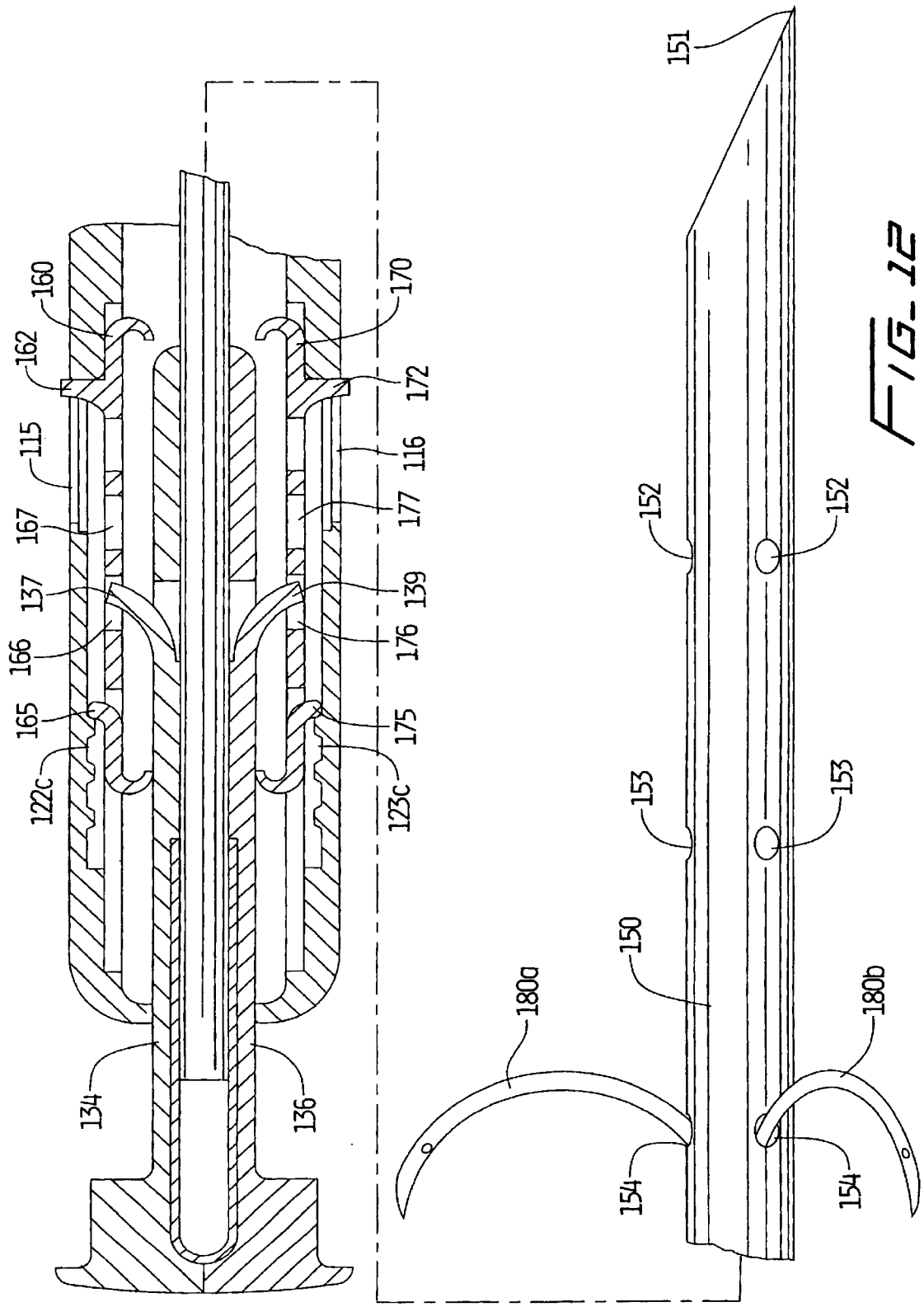
FIG. 12 is a longitudinal cross-sectional view similar to FIG. 8 except showing the plunger engaging the proximal openings in the ratchet and in an advanced position and the tines advanced to a fully deployed position through the proximal windows of the needle.

After ablation fluid is injected through the tines 180 at one or more of their three radial positions through intermediate windows 153, the plunger 130 can once again be retracted in a proximal direction to pull the ratchets 160, 170 proximally via engagement of plunger tabs 137, 139 with walls 167*b*, 177*b* of intermediate apertures 167, 177. Plunger tabs 137, 139 slide out of apertures 167, 177 and into proximal apertures 166, 176 of ratchets 160, 170, respectively. Plunger 130 can then once again be advanced, forcing ratchets 170, 190 distally, to deploy the tines 180 through proximal windows 154 of the needle 150 (FIG. 12), with flexible retention tabs 165, 175 functioning to retain the tines 180 in their radially deployed position and indicator tabs 162, 172 functioning to indicate the radial position of the tines 180 to the user. As can be appreciated, the extent of distal advancement of the plunger 130 will determine the extent of radial deployment of the tines 180 (e.g. first, second, third deployed positions). FIG. 12 illustrates the plunger 130 in the distalmost position corresponding to full deployment of tines 180 through proximal windows 154 of needle 150. Ablation fluid can be injected through tines in one or more of their radial positions.

Note that if the tines 180 are composed of shape memory metal, cold saline would be injected during retraction and advancement of the tines 180 from the needle 150 to maintain the tines in the martensitic state as discussed above.

Although three positions of the tines are shown, fewer or additional positions are contemplated. Moreover, fewer or greater number of windows can be provided in the needle 150.

Figure 13:
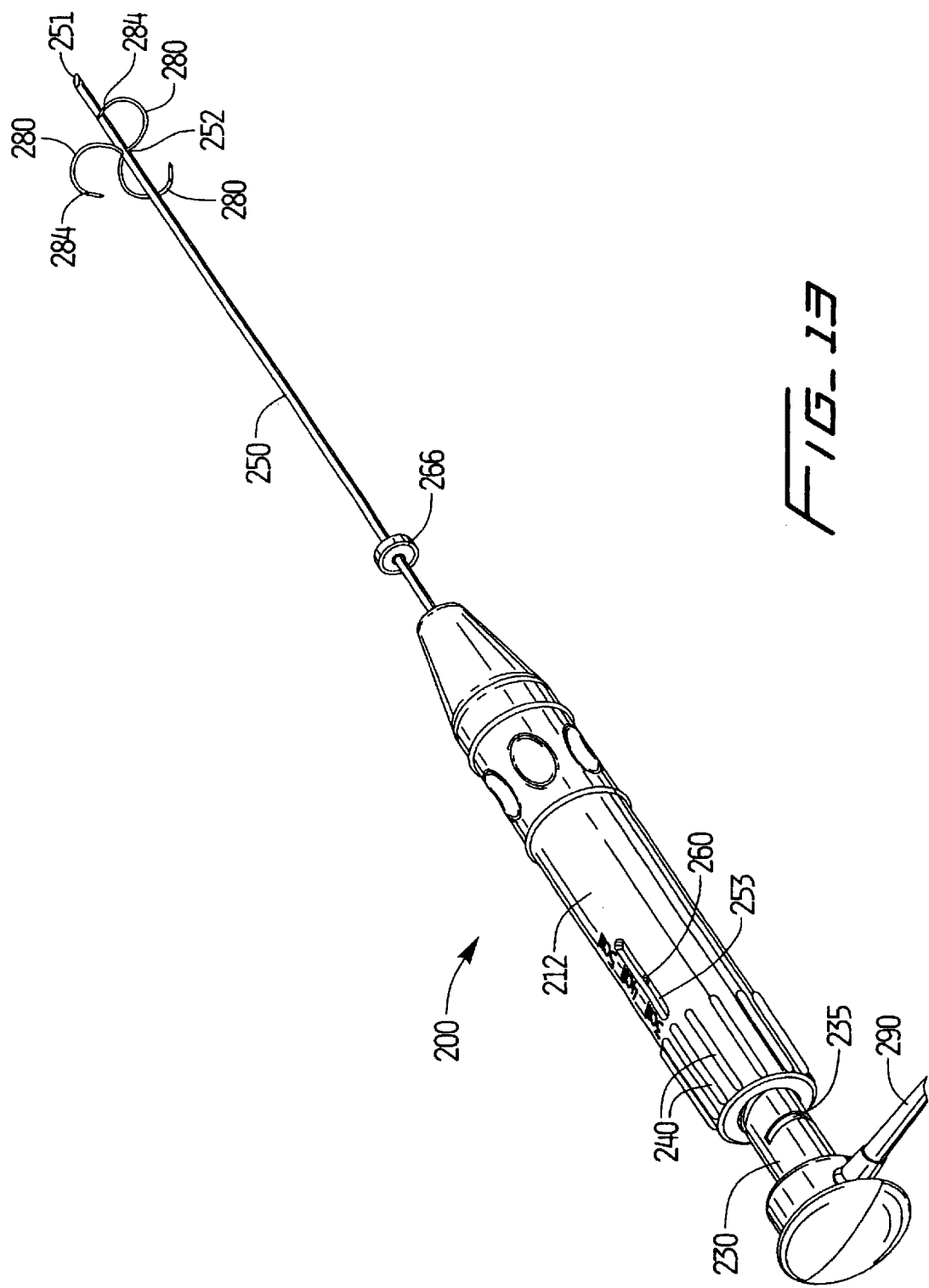
FIG. 13 is a perspective view of another alternate embodiment of the apparatus of the present invention showing the fluid delivery members (tines) in the fully deployed position.
Figure 14:
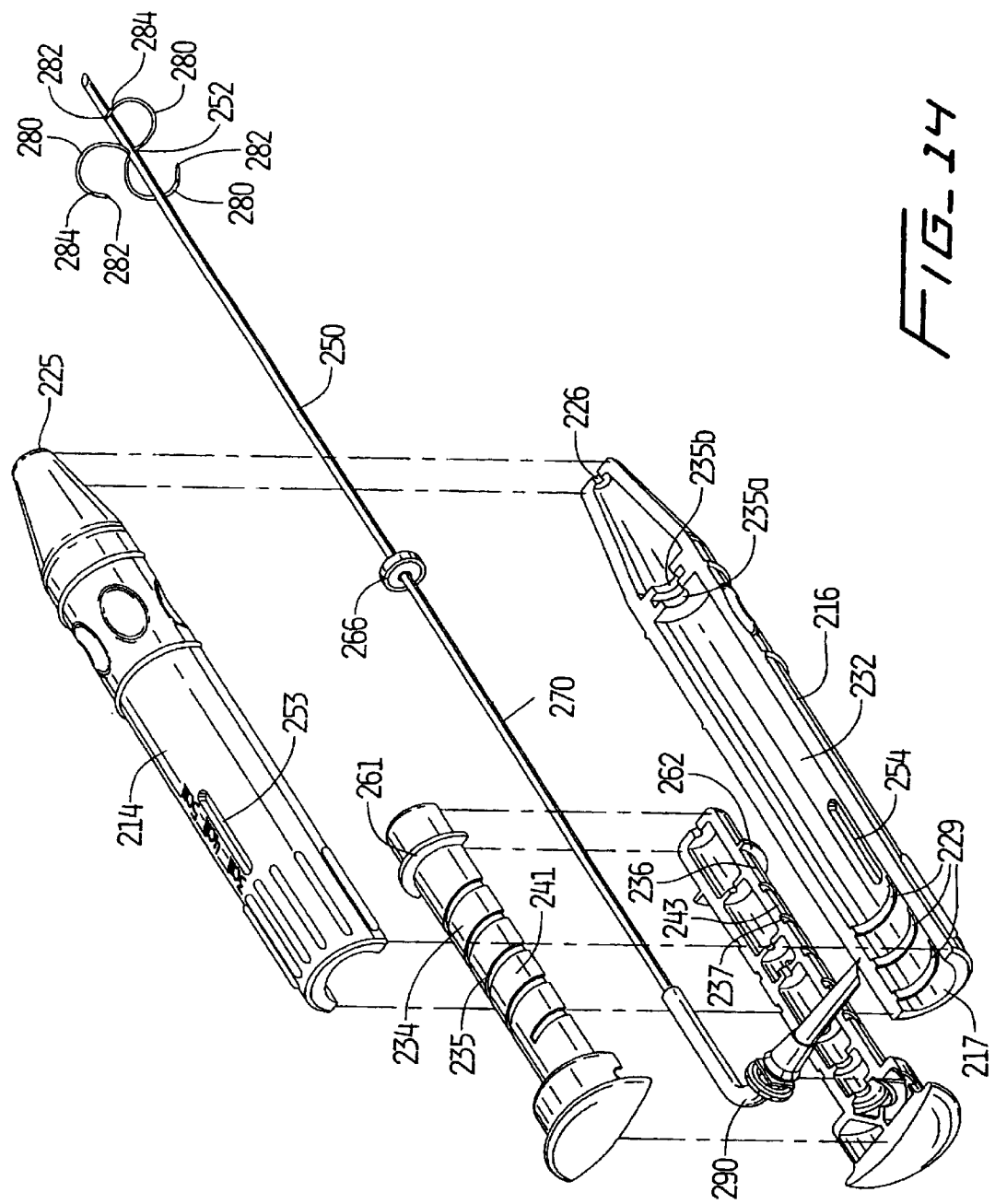
FIG. 14 is an exploded view of the apparatus of FIG. 13.
Figure 15:
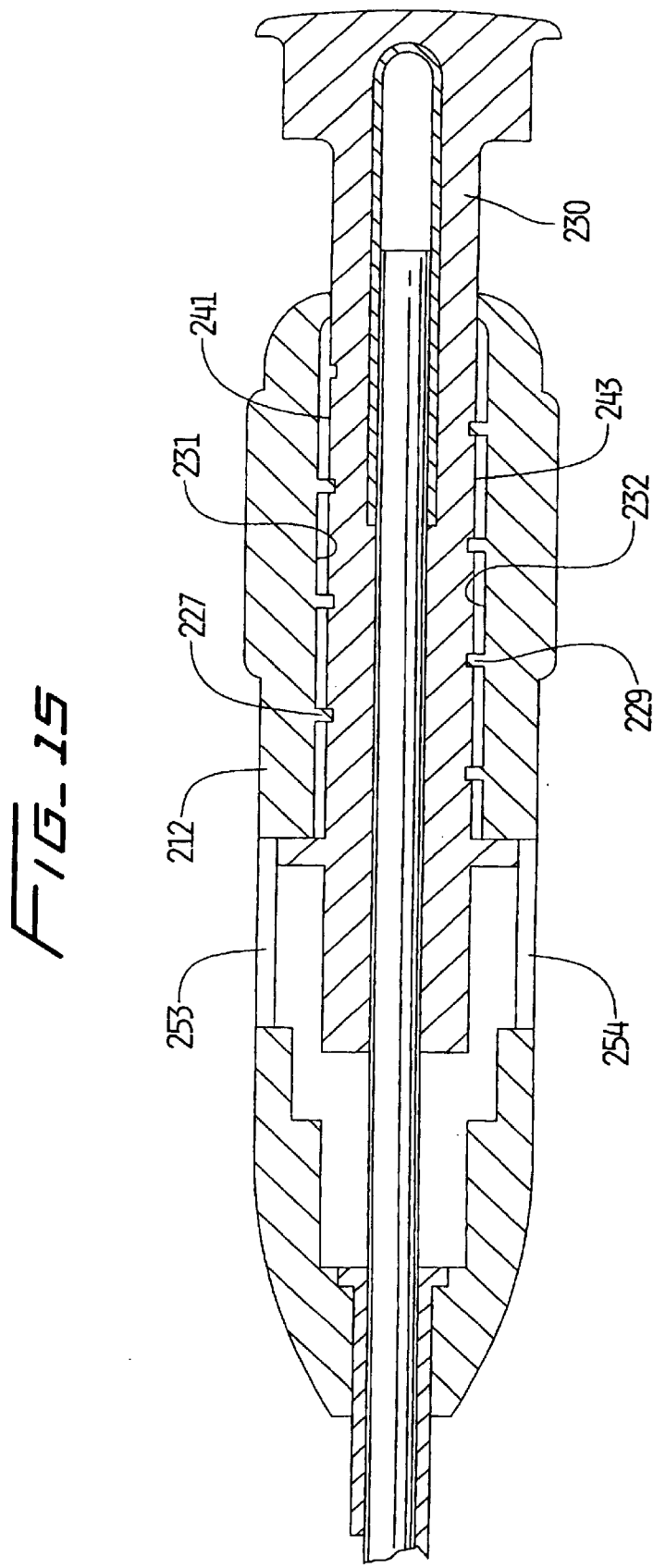
FIG. 15 is a longitudinal cross-sectional view of the plunger and housing of FIG. 13 showing the plunger in the initial position.

FIGS. 13–15 illustrate another alternate embodiment of the apparatus of the present invention for delivering ablation fluid. The tines (fluid delivery members) 280 of the apparatus 200 of this embodiment are deployed in an arcuate path by rotation of threaded actuator 230.

More specifically, and with reference to the exploded view of FIG. 14, apparatus 200 has an actuator 230 and a housing 212 composed of two identical housing halves 214 and 216. Each housing half 214, 216 has a proximal opening 215, 217 for receiving tubing 290, a distal opening 225, 226 for receiving needle 250, and a series of partial threads 227, 229, on a respective inner surface 231, 232. Recesses 235*a*, 235*b* in housing halves 216, and identical recesses in housing half 214, are dimensioned to receive a proximal portion of needle 250. Longitudinal ribs 240 on the other surface of housing 212 facilitate grasping by the user.

Elongated member or needle 250 extends from distal openings 225, 226 of housing 212. Three tines 280 are contained within the needle 250 in a substantially straight retracted position and are deployable radially from the needle 250 through the three windows (openings) 252 with the extent of radial deployment dependent on the degree of rotation of the actuator 230. The tines 280 are shown in FIGS. 13 and 14 in a fully deployed position. Each of the tines 280 preferably has a sharp distal tip 282 for penetrating tissue and a series (preferably three) of openings 284 in the sidewall communicating with the internal lumen to deliver ablation fluid. Although three tines are shown a fewer or greater number are also contemplated as are a fewer or greater number of sidewall openings.

Actuator 230 is composed of first and second actuator halves 234, 236, each having a series of threads 235, 237 on the outer surface 241, 243, respectively. External threads 235, 237 are engageable with the partial threads 227, 229 of housing halves 214, 216. The inner support tube 270 is mounted within actuator 230, preferably captured in recesses formed between ribs, as in the embodiments described above. Inner tube 270 is connected to tines 280 and is slidable and rotatable within needle 250. The lumen of inner tube 270 communicates with the lumen of the tines 280. Needle 250 is fixed within recesses 235*a*, 235*b* of housing half 216 and corresponding recesses in housing half 214. Tubing 290 extends through the proximal openings in actuator 230 and is mounted over inner tube 270 so that the lumen of tubing 290 is in fluid communication with the lumen of inner tube 270. Consequently, ablation fluid can be delivered through tubing 290 into inner tube 270 and through the lumens of the tines 280, exiting sidewall openings 284 of tines 280 into the tissue.

Since tines 280 are fixedly mounted to inner tube 270, axial and rotational movement of inner tube 270 as a result of movement of actuator 230 likewise slides and rotates tines 280. Tines 280 are rotatable through windows (openings) 252 formed in the sidewall of needle 250 as shown. That is, as the actuator 230 is rotated it is advanced distally along the threads to rotate the tines 280 out of the openings 252 in needle 250. Further rotation and distal advancement of the actuator 230 advances the tines 280 further radially with respect to needle 250.

As noted above, tubing 290 is mounted over inner tube 270 to provide ablation fluid through mounting tube 270 and through the tines 280. Tubing 290 can also be used to deliver saline to maintain the tines 280 in a martensitic state within the needle 250 as described above.

An indicator collar 260, formed by half rings 261, 262 on actuator halves 234, 236, is mounted on actuator 230 to indicate the degree of radial deployment of the tines 280. As shown, housing halves 212 and 214 each have a window 253, 254, respectively, with markings, e.g. 3 cm, 4 cm and 5 cm. As the actuator 230 is rotated and advanced axially, the collar 260 is visible in windows 253, 254 adjacent the marking indicating the extent of deployment of the tines 280 from the needle 250, e.g. 3 cm, 4 cm, 5 cm. Other indicators are also contemplated.

A marking ring 266 is mounted on needle 250 to provide a depth indicator of the apparatus 200. A series of markings (not shown) can be provided along the length of the needle 250 to indicate the depth of penetration, i.e. the distance from the distalmost tip 251 of the needle 250 to the marking ring 266. Prior to insertion, the surgeon would slide the marking ring 266 along the needle 250 to align with the desired depth marking on the needle 250 (not shown). This would define the extent of penetration since the surgeon would insert the apparatus 200 until resistance was felt by the marking ring 260 against the skin.

In use, in the initial position, actuator 230 is in a retracted position with respect to housing 212. In this retracted position, the tines 280 are in a substantially straight position within needle 250 as cool saline is injected through the tines. The needle 250 is inserted into the body (with depth marking ring 266 adjusted to the desired depth) until the surgeon feels the slight resistance of the ring 266 against the skin. Once in the desired position, actuator 230 is rotated counterclockwise to advance the actuator 230 along the threads, thus axially advancing the inner tube 270 and attached tines 280. As advanced in this rotational motion, tines 280 rotate through apertures 252 in the needle 250 to assume the curved configuration shown in FIG. 14.

Ablation fluid is then injected through tubing 290 into the tines 280 (via inner 270) to treat the lesion. If it is desired to ablate a larger radial area of tissue, actuator 230 can be rotated further, advancing further distally with respect to housing 212 to further rotate and thereby extend the tines 280 further from housing 212. As actuator 230 is advanced, marker ring 260 appears in the windows 253, 254 adjacent the markings, e.g. 3 cm, 4 cm, etc., to indicate to the user the degree of deployment of the tines 280. It is also contemplated that the apparatus 200 could be provided with a detent or other structure to provide a tactile feel to the surgeon when the tines 280 are in each of the positions. After fluid delivery, actuator 230 is rotated in a reverse direction, thereby moving actuator 230 proximally along the threads, and rotating tines 280 in the reverse direction and back within the confines of needle 250.

FIG. 16 illustrates a distal portion of the needle of another alternate embodiment of the present invention. Apparatus 300 has a needle 302 with multiple sets of windows (openings) 304 axially displaced along the needle 302. The windows form exit apertures for the fluid delivery members (tines) 306. As shown, as the tines 306 extend through windows 304, they curve outwardly and distally towards the tip of the needle 304. Thus, they have a longitudinal directional component extending somewhat parallel to the longitudinal axis of the needle 302. The tines 306 can be deployed through each of the windows in a similar fashion as described above and like the tines described above have a series of openings 308 for fluid delivery and a sharp distal tip. Various number of windows can be provided in each set and a different number of sets of windows can be utilized in addition to that illustrated in FIG. 16 as well as in the embodiment of FIG. 17 described below.

In the embodiment of FIG. 17, which shows only the distal end of apparatus 350, needle 352 has multiple sets of axially displaced windows 354. In this embodiment, two or more tines 356, 356' can be deployed through each of the windows 354. The tines 356, 356' have sharp distal tips and a series of openings 358 for fluid delivery.

The apparatus can further be configured so that the tines extending through each window have a different radius of curvature as shown in FIG. 17. That is, in this embodiment, the two tines 356, 356' extending through each window 354 have a different radius of curvature and are axially displaced. The more proximal tine 356' extending through the window 354 has a smaller radius of curvature so that the tips 359, 359' of the tines 356, 356', respectively, are axially displaced to create a larger spherical ablation zone.

It is contemplated that the various apparatus of the present invention described above inject acetic acid into the tumor to ablate the tumor. The acetic acid diffuses into the cancerous cells, burning through the tumor septi, i.e. the compartments within the tumor, to produce immediate necrosis due to effects of cellular dehydration and protein denaturation followed by small vessel thrombosis. The volume of acetic acid and the number of infusions can vary. However, it is also contemplated that the apparatus of the present invention can be used to deliver other fluids such as hot saline or ethanol to ablate the tissue. Also, although contemplated for treating hepatic (liver) tumors, it is also contemplated that the apparatus can be utilized to treat tumors in other regions of the body such as the spleen, pancreas, or brain. The apparatus can also be used to inject other fluids, e.g. therapeutic fluids such as chemotherapeutic agents or gene cells.

While the above description contains many specifics, those specifics should not be construed as limitations on the scope of the disclosure, but merely as exemplifications of preferred embodiments thereof. For example, the flexible retention tab can be positioned on the housing and the series of recesses positioned on the plunger. Those skilled in the art will envision many other possible variations that are within the scope and spirit of the disclosure as defined by the claims appended hereto.

What is claimed is:

1. A surgical apparatus for delivering fluid to treat a lesion comprising:

an elongated member having a distal tip and a first and second set of openings formed in a sidewall proximal of the distal tip, the second set of openings being positioned proximally of the first set of openings;

first and second fluid delivery members movably positioned in the elongated member, each of the fluid delivery members having a lumen and at least one opening communicating with the lumen for delivering fluid to the lesion; and an actuator operatively associated with the fluid delivery members, the actuator actuable to a first position to move the fluid delivery members from a retracted position within the elongated member to a first deployed position extending radially with respect to the elongated member, the actuator further actuable to a second position to move the fluid delivery members from the first deployed position to a second deployed position extending further radially from the elongated member, the fluid delivery members being retained in the first and second deployed positions by a first and second radially spaced ratchets.

2. The apparatus of claim 1, wherein the distal tip of the elongated member is a sharp tip configured to penetrate tissue.

3. The apparatus of claim 2, wherein each of the fluid delivery members has a sharp tip configured to penetrate tissue.

4. The apparatus of claim 1, wherein the actuator is movable axially to move the fluid delivery members to the first deployed position, the fluid delivery members connected to an elongated tube operatively connected to the actuator.

5. The apparatus of claim 1, wherein the actuator is movable to first and second axial positions, wherein in the first axial position the fluid delivery members are deployable through the first set of openings and in the second axial position the fluid delivery members are deployable through the second set of openings.

6. The apparatus of claim 1, wherein the ratchets are slidable distally.

7. The apparatus of claim 1, further comprising an indicator on the ratchet to indicate the position of the fluid delivery members.

8. The apparatus of claim 1, further comprising an indicator to provide an indication of the deployed positions of the fluid delivery members.

9. The apparatus of claim 1, wherein the ratchet includes a plurality of apertures to receive a tab of the actuator.

10. A surgical apparatus for delivering fluid to treat a lesion comprising:

an elongated member having a distal tip and a first and second set of openings formed in a sidewall proximal of the distal tip, the second set of openings being positioned proximally of the first set of openings;

a plurality of fluid delivery members movably positioned in the elongated member, each of the fluid delivery members having a lumen and at least one opening communicating with the lumen for delivering fluid to the lesion; and an actuator operatively associated with the fluid delivery members, the actuator actuable to a first position to move the fluid delivery members from a retracted position within the elongated member to a first deployed position extending through the first set of openings and radially with respect to the elongated member to treat a first portion of the lesion, the actuator actuable to retract the fluid delivery members from the first set of openings and further actuable to a second position to move the fluid delivery members to a second deployed position extending through the second set of openings and radially with respect to the elongated member to treat a second portion of the lesion proximal of the first portion, the actuator engagable with a movable ratchet to deploy and retain the fluid delivery members.

11. The apparatus of claim 10, further comprising an indicator to provide a visual indication of the position of the fluid delivery members.

12. The apparatus of claim 10, wherein the ratchet is slidable distally and proximally.

13. The apparatus of claim 12, wherein the actuator includes a tab engagable with the ratchet and extendable through a respective opening in the ratchet, the ratchet having a tab to retain the fluid delivery members in one of the first and second deployed positions.

14. The apparatus of claim 10, wherein the elongated member comprises a third set of openings positioned proximally of the second set of openings, the actuator actuable to a third position to move the fluid delivery members through the third set of openings.

15. The apparatus of claim 14, wherein the fluid delivery members are movable to a plurality of radial positions with respect to the elongated member through each set of openings.

16. The apparatus of claim 10, wherein the ratchet includes a plurality of apertures to receive a tab of the actuator.

17. A surgical apparatus for delivering fluid to treat a lesion comprising:

an elongated member having a distal tip and a first and second set of openings formed in a sidewall proximal of the distal tip, the second set of openings being positioned proximally of the first set of openings;

a plurality of fluid delivery members movably positioned in the elongated member, each of the fluid delivery members having lumen and at least one opening communicating with the lumen for delivering fluid to the lesion; and an actuator operatively associated with the fluid delivery members, the actuator actuable to a first position to move the fluid delivery members from a retracted position within the elongated member to a first deployed position extending through the first set of openings and radially with respect to the elongated member to treat a first portion of the lesion, the actuator further actuable to a second position to move the fluid delivery members to a second deployed position extending through the second set of openings and radially with respect to the elongated member to treat a second portion of the lesion proximal of the first portion;

wherein the fluid delivery members are movable to a plurality of radial positions with respect to the elongated member through each set of openings, a ratchet to retain the fluid delivery members in the deployed position.

18. The apparatus of claim 15, further comprising an indicator to provide an indication of the deployed positions and the radial positions of the fluid delivery members.

* * * * *